United States Patent [19]

Pintschovius et al.

[11] 4,263,441
[45] Apr. 21, 1981

[54] NOVEL FLUORINE-CONTAINING BENZ-AZOLE DERIVATIVES, PROCESS FOR THEIR MANUFACTURE AND THEIR USE AS OPTICAL BRIGHTENERS

[75] Inventors: Ulrich Pintschovius, Hattersheim am Main; Erich Schinzel, Hofheim am Taunus; Günter Rösch, Bad Soden am Taunus, all of Fed. Rep. of Germany

[73] Assignee: Hoechst Aktiengesellschaft, Fed. Rep. of Germany

[21] Appl. No.: 959,924

[22] Filed: Nov. 13, 1978

[30] Foreign Application Priority Data

Nov. 15, 1977 [DE] Fed. Rep. of Germany ....... 2750947

[51] Int. Cl.³ ............... C07D 263/062; C07D 277/66; C09K 11/06; C09K 9/02
[52] U.S. Cl. .......................... 548/220; 252/301.28; 106/288 Q; 548/305; 564/156
[58] Field of Search .................... 260/307 D; 548/220

[56] References Cited

U.S. PATENT DOCUMENTS

| | | | |
|---|---|---|---|
| 3,314,894 | 4/1967 | Nyilas | 260/307 D |
| 3,336,330 | 8/1967 | Schinzel | 260/307 D |
| 3,798,231 | 3/1974 | Fleck | 260/307 D |

FOREIGN PATENT DOCUMENTS 2695301  4/1977  Fed. Rep. of Germany .

*Primary Examiner*—Mark L. Berch
*Attorney, Agent, or Firm*—Connolly and Hutz

[57] ABSTRACT

Compounds of the general formula

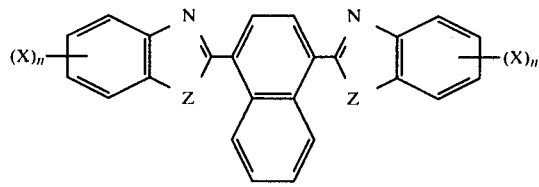

in which X represents a trifluoromethyl group or a fluorine atom, n is 1 or 2, Z is an oxygen atom or a NR grouping, in which R is hydrogen or an optionally substituted alkyl group, the benzo rings optionally containing further nonchromophoric substituents. These compounds may be prepared by reacting the dichloride of 1,4-naphthalene-dicarboxylic acid with 2 mols of an o-aminophenol or of an o-nitroaniline and by subsequently cyclizing the acylamino compound obtained. The products are suitable as optical brighteners.

2 Claims, No Drawings

NOVEL FLUORINE-CONTAINING BENZ-AZOLE DERIVATIVES, PROCESS FOR THEIR MANUFACTURE AND THEIR USE AS OPTICAL BRIGHTENERS

The present invention relates to novel fluorine-containing benz-azole derivatives, a process for their manufacture and their use as optical brighteners.

The present invention provides novel 1,4-bis[benzazolyl]-napthalenes which are colorless or slightly yellow and which show in solution a more or less pronounced reddish-blue to greenish-blue fluorescence and have the general formula I.

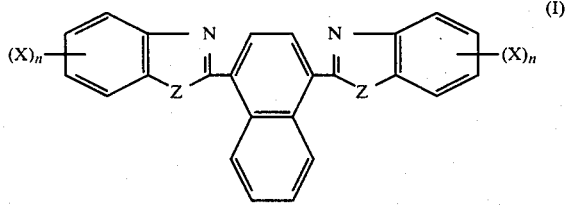

in which X is a trifluoromethyl group or a fluorine atom, n is the integer 1 or 2, Z is an oxygen atom or a NR grouping, wherein R represents hydrogen or a lower, optionally substituted, alkyl group, with further non-chromophoric substituents also possibly being present in the benzo rings. As non-chromophoric substituents of this kind there may be mentioned, for example, lower alkyl, lower alkoxy, halogen, cyano groups, carbo-lower alkoxy groups, phenyl or benzyl groups. The benzo rings may carry one or two of these non-chromophoric substituents. The term "lower" means in this case those groups which contain from 1 to 4 carbon atoms.

The benzoxazolyl compounds of the invention (Z=O) may be synthetized according to the preparation process illustrated in the following, in which X and n are defined as in formula I.

The dichloride of naphthalene-1,4-dicarboxylic acid IV is condensed with at least 2 mols of o-amino-phenols of the general formula

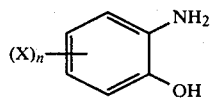

preferably in the presence of a base, and the bis-acylamino compounds obtained which correspond to the general formula

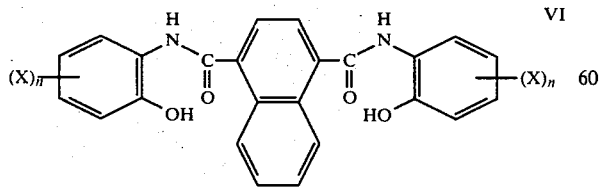

are cyclized in an inert gas atmosphere in high-boiling solvents and in the presence of catalysts, to give the compounds of the invention (I, Z=O).

As o-aminophenols of the formula V there may be used, for example:
3-Trifluoromethyl-2-amino-phenol, 4-trifluoromethyl-2-amino-phenol, 5-trifluoromethyl-2-amino-phenol, 6-trifluoromethyl-2-amino-phenol, 3,5-di-(trifluoromethyl)-2-amino-phenol), 4-fluoro-2-amino-phenol, 5-fluoro-2-amino-phenol, 4,6-difluoro-2-amino-phenol, 4-methyl-5-flouro-2-amino-phenol, 5-methyl-4-fluoro-2-amino-phenol.

As high-boiling solvents for the ring closure reaction there may be mentioned, for example: 1,2,4-Trichlorobenzene, trichlorobenzene mixtures, chloronaphthalenes, tetraline or methylnaphthalene mixtures. The reaction temperature for the cyclization is in the range of from 150° to 260° C., preferably from 200° to 230° C. As ring closure catalysts there may be used acids, including Lewis acids, such as zinc chloride, p-toluenesulfonic acid or boric acid.

The benzimidazole compounds (Z=NR) of the invention may be obtained in accordance with the preparation process illustrated in the following, in which process X, R and n are defined as under formula I. The dichloride of the naphthalene-1,4-dicarboxylic acid IV is condensed with at least 2 mols of o-nitroanilines of the general formula

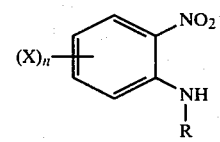

preferably in the presence of a base, the bis-nitroacylamino compounds obtained which have the general formula

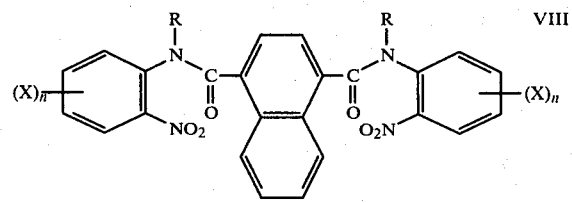

are reduced according to known methods by means of catalyst with hydrogen or another reducing agent in an appropriate solvent to give the corresponding bis-o-aminoacylamines

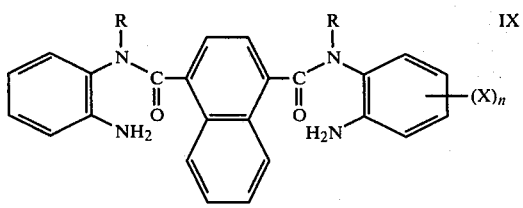

and these latter are then cyclized by the action of acids to give the compounds of the invention (Z=NR). This ring closure reaction is effected at a temperature of from about 100° to 120° C. in an inert organic solvent, such as benzene, toluene, chlorobenzene in the presence of acids, such as toluene-sulfonic acid. The cyclization is carried out preferably in boiling glacial acetic acid.

If the starting compounds of the formula VII contain an electronegative group in the para position to the nitro group, it is recommended to first reduce said o-nitroaniline to the corresponding o-phenylene diamine and thereafter to react and/or cyclize it with the naphthalene-1,4-dicarboxylic acid chloride, as has been described above. In the reaction sequence described above, the group R is introduced by using a N-substituted o-nitroaniline. Besides, it is also possible to introduce this group after the cyclization by a corresponding alkylation at the nitrogen atom according to known methods.

The acylation of the o-aminophenols of the formula IV and the o-nitroanilines of the formula VII is generally effected under the same conditions at a temperature of up to about 100° C., preferably from 70° to 80° C. in an inert organic solvent, such as benzene, dioxan, toluene, dichloroethane or toluene in the presence of a base of, for example, a trialkylamine.

As o-nitro-anilines of the general formula VII there may be used, for example:
3-Trifluoromethyl-2-nitro-aniline, 4-trifluoromethyl-2-nitro-aniline, 5-trifluoromethyl-2-nitro-aniline, 3,5-bis-(trifluoromethyl)-2-nitro-aniline, 4-fluoro-2-nitro-aniline, 4,6-difluoro-2-nitro-aniline, 4-trifluoromethyl-2-nitro-methylaniline, 4-trifluoromethyl-2-nitro-ethylaniline.

Due to their fluorescence properties, the novel compounds of the invention may be used in a wide field of application. They serve above all for the optical brightening of various natural and synthetic organic materials. This includes also those organic materials which may be used for the processing of mineral substances, for example of inorganic pigments.

As substrated to be brightened there may be mentioned, for example, the following materials: Synthetic fibers, for example those of acetyl cellulose, polyesters, such as polyethylene terephthalate, polyamides, polyolefins, polyvinyl chloride, polyvinylidene chloride and polyacrylonitrile, as well as sheets, films, ribbons and shaped articles made from these materials.

The compounds of the invention may be used in the form of solutions in organic solvents or in an aqueous (acid) solution or dispersion, advantageously with the aid of a dispersing agent.

As dispersing agents there may be used, for example, soaps, polyglycol ethers derived from fatty alcohols, fatty amines or alkylphenols, cellulose sulfite waste liquors or condensation products of optionally alkylated naphthalene-sulfonic acids with formaldehyde as well as polyvinyl acohols.

The brightening of the fiber material with the aqueous or optionally organic brightening liquor is carried out either according to the exhaustion process at temperatures of preferably from about 20° to 150° C. or under thermosol conditions, the textile material being, for example, impregnated or sprayed with the brightening solution and/or dispersion and being squeezed, for example between rollers, to a residual moisture content of from about 50 to 120 %. Subsequently the textile material is subjected for a period of from about 10 to about 300 seconds to a heat treatment, preferably by way of dry heat, at a temperature of from about 120° to 240° C. This thermosol process may be combined with other finishing operations, for example the application of synthetic resin in order to obtain easy-care properties, the material optionally being condensed, after the impregnation and drying at a temperature of from 100° to 150° C., for a period of from 5 to 20 minutes at 150° to 200° C., to achieve the cross-linking.

The compounds of the general formula (I) may also be added to detergents. These latter may contain the common fillers and auxiliaries, such as alkali metal silicates, alkali metal phosphates and/or condensed phosphates, alkali metal borates, alkali metal salts of carboxymethyl cellulose, foam stabilizers, such as alkanolamides of higher fatty acids, or complex forming agents, such as soluble salts of ethylene-diamine-tetraacetic acid or diethylene-triamine-pentaacetic acid, as well as chemical bleaching agents, such as perborates or percarbonates, perborate activators of the polyacetic acid amide type, which in conjunction with the peroxo compounds lead to the splitting-off of peracetic acid, and disinfectants.

The compounds of the invention may furthermore be added to high molecular weight organic materials before or during their processing. Thus, for example, when manufacturing fibers, films, sheets, ribbons, plates or other shaped articles, they may added to the plastics powders, thermoplastic compositions, melts, polymer solutions or dispersions, for example they may be dissolved in the spinning mass prior to spinning. Suitable compounds may also be added to the low molecular weight starting materials prior to the polycondensation or polymerization of, for example, polyamide-6, polyamide-6,6 or linear polyesters of the polyethyleneglycol-terephthalate type.

The compounds of the invention yield on polyacrylonitrile and polyacrylonitrile copolymers particularly high degrees of whiteness, if said compounds are employed in the presence of bleaching agents, such as sodium chlorite, in the acid range at a pH value of from 2 to 5. A special advantage of the products of the invention is to be seen in the insignificant influence of a change of the pH value in the specified range on the brightening effects.

The amount of the compounds of the general formula to be used according to the invention, calculated on the material to be optically brightened, may vary wide limits, depending on the field of application and the intended effect. It may be determined easily by simple preliminary tests and is generally in the range of from about 0.01 to about 2%, preferably from 0.02 to 0.2%, calculated on the material to be brightened.

The following Examples further illustrate the invention. The temperatures have been given in degrees Celsius, the percentages being by weight, unless otherwise stated.

TABLE 1

Compound of the formula

| No. | n | Substituent X | pos | Melting point | Absorption in DMF solution λ [nm] | ε | Fluorescence in DMF sol. |
|---|---|---|---|---|---|---|---|
| 101 | 1 | CF$_3$ | 4 | 275–276.5° | 376 | 33 | 100 | bluish violet |
| 102 | 1 | CF$_3$ | 5 | 212–214° | 372 | 31 | 600 | violet |
| 103 | 1 | CF$_3$ | 6 | 221–222° | 373 | 31 | 600 | bluish violet |
| 104 | 2 | (CF$_3$)$_2$ | 4,6 | 201–203° | 378 | 30 | 300 | blue |
| 105 | 1 | F | 5 | 228–230° | 376 | 32 | 600 | bluish |

TABLE 1-continued

Compound of the formula $(X)_n$-[benzoxazole]-naphthalene-[benzoxazole]-$(X)_n$ (positions 3,4,5,6,7 on rings, with N and O in oxazole rings)

| No. | Substituent n X pos | Melting point | Absorption in DMF solution λ [nm] ε | Fluorescence in DMF sol. |
|---|---|---|---|---|

106  1,4-Bis-(5-methyl-6-fluorobenzoxazolyl-2)-naphthalene; m.p. 266–268° C., absorption in DMF: λ 378 nm, ε 36 300; fluorescence bluish violet.

TABLE 2

Compound of the formula $F_3C$-[benzimidazole(N-R)]-naphthalene-[benzimidazole(N-R)]-$CF_3$

| No. | Substituent R | M.p. | Absorption in DMF sol. λ [nm] ε | Fluorescence in DMF sol. |
|---|---|---|---|---|
| 110 | H | 317–318° | 346    28 600 | bluish viol. |
| 111 | $C_2H_5$ | 297–298° | 304    20 800 | violet |
| 112 | $CH_3$ | 351–352° | 310    22 700 | violet |

EXAMPLE 1:

The preparation of compound 102 (Table 1) is carried out as follows:

Starting from 21.6 g of naphthalene-1,4-dicarboxylic acid and 28 g of thionyl chloride, the dichloride is prepared in 78 g of toluene. After elimination of the excess thionyl chloride, the acid chloride solution is added dropwise at 80° C. to a solution of 34.8 g of 4-trifluoromethyl-2-amino-phenyl, 24.4 ml of N,N-dimethyl-aniline and 80 ml of dioxan, and stirring is continued for 5 hours at this temperature. Then the reaction mixture is distilled with water vapor, the precipitate is filtered off with suction and washed with diluted hydrochloric acid and water. After drying, 53.1 g of acylamino compound are obtained, which compound has a melting point (with decomp.) of from 262° to 264° C.

53 Grams of the above-mentioned acylamino compound are heated for 75 minutes at a temperature of from 200° to 215° C., in a nitrogen atmosphere in 300 ml of trichlorobenzene in the presence of 0.18 g of p-toluene-sulfonic acid, in which process the water having been split off passes over with a small amount of trichlorobenzene. After the main amount of the solvent (about 200 ml) has been distilled off, 300 ml of methanol are added. By suction-filtration, washing with methanol and drying, 31.8 g of benzoxazole (102) are obtained as a yellow crystalline powder.

After recrystallization from toluene and DMF the melting point is in the range of from 212° to 214° C.

In the same manner, compounds 101, 103, 104 and 105 from Table 1 may be synthetized.

EXAMPLE 2:

Preparation of 1,4-bis-[5-trifluoromethyl-benzimidazolyl-(2)]-naphthalene (compound 110)

A solution of 25.3 g of naphthalene-1,4-dicarboxylic acid chloride in 90 ml of toluene is added, while stirring, at 80° C. to a mixture of 42 g of 4-trifluoromethyl-2-nitro-aniline, 26 ml of N,N-dimethylaniline and 100 ml of dioxan, the mixture have been preheated under nitrogen to 70° C.

After 5 hours of stirring at 80° C., the reaction mixture is distilled with water vapor, the acylamino compound in the residue is filtered off with suction and washed with diluted hydrochloric acid and water. After the product has been dried, 49.4 g of an ocher-colored powder are obtained, which has a crude melting point of from 233° to 236° C.

49.3 Grams of this o-nitroacylamino compound are reduced in 450 ml of DMF in the presence of 6.0 g of Raney nickel at 50° C. with hydrogen. After having removed the catalyst by suction-filtration, the filtrate is concentrated almost to dryness, is dissolved in 150 ml of glacial acetic acid and boiled under reflux for 3 hours, in which process the benzimidazole cyclization takes place. The benzimidazole formed is precipitated by adding 100 g of water (34 g). By recrystallizing the product several times from dichloroethane and acetonitrile, compound 110 is obtained as a colorless powder having a melting point of from 317° to 318° C.

EXAMPLE 3

Preparation of 1,4-bis-[5-trifluoromethyl-1-ethyl-benzimidazolyl-(2)]-naphthalene (compound 111)

At first, 3-nitro-4-ethylamino-benzotrifluoride is prepared from 4-chloro-3-nitrobenzotrifluoride and ethylamine according to Geman Offenlegungsschrift No. 2 018 232, Example 1), and the former product is catalytically reduced in ethanol to give the 3-amino-4-ethylamino-benzotrifluoride colorless crystals of a melting point of from 72° to 74° C.

42.5 Grams of this diamino compound are dissolved under a nitrogen atmosphere with 26 ml of dimethylaniline and 100 ml of dioxan; subsequently a solution of 25.3 g of naphthalene-1,4-dicarboxylic acid chloride in 80 ml of toluene is added at a temperature of from 25° to 45° C., and stirring is continued for 2 hours at 70° C. After a steam distillation the separated product is filtered off with suction, washed with water and dried. The acylamino compound obtained (56.7 g) is continued to be stirred for 2 hours with 150 ml of glacial acetic acid at 118° C. 51 Grams of raw product can be precipitated by stirring the mixture into water. Compound (111) can be obtained in a pure form as colorless crystals by a recrystallization from 200 ml of DMF. Melting point; 297° to 298° C.

For the application onto textile material, 100 mg each of these brighteners were dissolved in 10 ml of dimethyl formamide under heat, and 5 ml of an emulsifier were added. This clear solution was introduced, while stirring, into 85 ml of water. Thus, a stable dispersion is obtained which contains 1 g/l of brightener.

APPLICATION EXAMPLE 1

A polyester fabric was impregnated with the above-described dispersion containing 1 g/l of compound 105, and said fabric was then squeezed between two rubber rolls to a residual moisture of 70 %. Thereafter the sample was dried in a stenter frame at 190° C. for 30 seconds and then fixed. Subsequently the fabric showed a white color that was considerably brighter than that of an untreated fabric.

APPLICATION EXAMPLE 2

Of a dispersion that had been prepared according to the method described above, which dispersion contained 1 g/l of compound 102, an amount was measured that the amount of brightener was 0.1 % of the weight, calculated on the substrate. This amount was added to an aqueous liquor which contained 2 g/l of a bleaching agent. A fabric of perlon taffeta was treated in this liquor in a ratio of 1:15 during 60 minutes at 98° C. After rinsing and drying, the fabric showed a markedly higher degree of whiteness than an untreated fabric.

APPLICATION EXAMPLE 3

Of the dispersion described above containing compound 110, an amount was measured which corresponded to an application of 0.1%, calculated on a polyacrylonitrile fabric. This amount was introduced into an aqueous liquor which contained 2 g/l of $NaClO_2$ and b 1 g/l of a stabilizer. This liquor was adjusted to a pH of 3.5 with acetic acid. The polyacrylonitrile fabric was treated with this liquor for 1 hour at 98° C. with a goods-to-liquor ratio of 1:15. After rinsing and drying the fabric, a considerably higher degree of whiteness could be observed.

APPLICATION EXAMPLE 4

30 Milligrams of compound 105 were dissolved in 25 g of a plasticizer and 1.5 g of a stabilizer. This mixture was added, while stirring, to 75 g of a stock mixture having the following composition:
75 g of polyvinyl chloride
2 of titanium dioxide
0.2 g of wax.
This mixture was rolled for 10 minutes on a roller frame at 160° C. The rolled sheet obtained showed a degree of whiteness of 128 (Berger) or 129 (Stensby). When using 30 mg of compound 102, the degrees of whiteness measured were 118 (Berger) and 121 (Stensby).

APPLICATION EXAMPLE 5

1.5 Grams of titanium dioxide and 0.03 g of compound 105 were added to 100 g of polystyrene granules and were evenly distributed on the surface of the granules, while stirring constantly. From the granules thus treated, injection molded pieces were manufactured, whose degree of whiteness was determined as being 126 (Berger) and 132 (Stensby). With injection molded pieces of the same composition, however, having a content of 0.03% of compound 102, following degrees of whiteness were determined:
115 (Berger); 124 (Stensby)

APPLICATION EXAMPLE 6

In the same manner as described in Application Example 5, injection molded pieces were manufactured from polypropylene granules having a content of 0.03% of brightener 105 or brightener 102. The following degrees of whiteness were measured:
Brightener 105=110 (Berger); 122 (Stensby)
brightener 102=113 (Berger); 124 (Stensby).

In the same manner, injection molded pieces were manufactured from polyester which already contained titanium dioxide and 0.03% of brightener 105 or 102. The following degrees of whiteness were determined:
Brightener 105=(Berger); 151 (Stensby)
brightener 102=152 (Berger); 152 (Stensby).

what is claimed is:

1. A compound of the formula

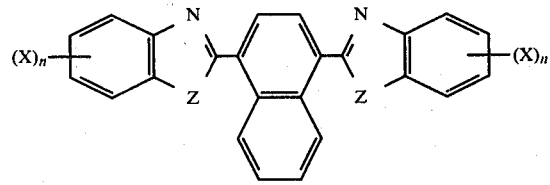

in which X is trifluoromethyl, n is the integer 1 or 2, Z is oxygen, and the benzo rings may be substituted by one or two lower alkyl, lower alkoxy, halogen, cyano, carbo-lower alkoxy, phenyl or benzyl.

2. A compound of the formula

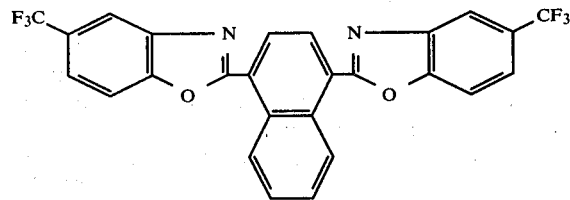

* * * * *